United States Patent
Hatakeyama et al.

(10) Patent No.: US 11,911,161 B2
(45) Date of Patent: Feb. 27, 2024

(54) BIOLOGICAL ELECTRODE AND MANUFACTURING METHOD THEREOF

(71) Applicant: SHIN-ETSU CHEMICAL CO., LTD., Tokyo (JP)

(72) Inventors: Jun Hatakeyama, Jyoetsu (JP); Motoaki Iwabuchi, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 736 days.

(21) Appl. No.: 17/061,762

(22) Filed: Oct. 2, 2020

(65) Prior Publication Data

US 2021/0015384 A1 Jan. 21, 2021

Related U.S. Application Data

(62) Division of application No. 15/427,680, filed on Feb. 8, 2017, now abandoned.

(30) Foreign Application Priority Data

Mar. 3, 2016 (JP) .................................. 2016-040873
Jul. 12, 2016 (JP) .................................. 2016-137840

(51) Int. Cl.
*A61B 5/25* (2021.01)

(52) U.S. Cl.
CPC .......... *A61B 5/25* (2021.01); *A61B 2562/028* (2013.01); *A61B 2562/0209* (2013.01); *A61B 2562/125* (2013.01)

(58) Field of Classification Search
CPC .................................. A61B 5/25; B05D 3/0254
See application file for complete search history.

(56) References Cited

U.S. PATENT DOCUMENTS

| 5,981,680 A | 11/1999 | Petroff et al. |
| 2002/0188069 A1 | 12/2002 | Sugo et al. |
| 2005/0107713 A1 | 5/2005 | Van Herk et al. |
| 2008/0079565 A1 | 4/2008 | Koyama |

FOREIGN PATENT DOCUMENTS

| CN | 102671294 A | 9/2012 |
| JP | H11-209714 A | 8/1999 |
| JP | 2002-332305 A | 11/2002 |

(Continued)

OTHER PUBLICATIONS

JP-2012205884-A Kokama English translation (Year: 2012).*

(Continued)

*Primary Examiner* — Jason L Vaughan
*Assistant Examiner* — Amanda Kreiling
(74) *Attorney, Agent, or Firm* — Oliff PLC

(57) ABSTRACT

The present invention provides a biological electrode including an electro-conductive base material and a living body contact layer formed on the electro-conductive base material; wherein the living body contact layer includes a resin layer and particles dispersed in the resin layer, the particles being coated with gold, silver, or platinum, and a thickness of the resin layer is equal to or thinner than an average particle size of the particles. The biological electrode of the present invention is superior in electric conductivity and biocompatibility, light in weight, and can be manufactured at low cost.

11 Claims, 2 Drawing Sheets

(56) References Cited

FOREIGN PATENT DOCUMENTS

| | | | |
|---|---|---|---|
| JP | 2004-033468 A | 2/2004 | |
| JP | 2005-521458 A | 7/2005 | |
| JP | 2005-320418 A | 11/2005 | |
| JP | 2006-156068 A | 6/2006 | |
| JP | 2008-109847 A | 5/2008 | |
| JP | 2011-079946 A | 4/2011 | |
| JP | 2011-204530 A | 10/2011 | |
| JP | 2012205884 A | 10/2012 | |
| JP | 2012205884 A | * | 10/2012 |
| JP | 2015-100673 A | 6/2015 | |
| JP | 2015-109268 A | 6/2015 | |
| JP | 2015109268 A | * | 6/2015 |
| TW | I375709 B | 11/2012 | |
| WO | 2013/039151 A1 | 3/2013 | |

OTHER PUBLICATIONS

JP-2015109268-A Nishioka (Year: 2015).*
Apr. 5, 2018 Korean Office Action issued in Korean Patent Application No. 10-2017-0026969.
Sep. 28, 2018 Korean Office Action issued in Korean Patent Application No. 10-2017-0026969.
Nov. 20, 2018 Office Action issued in Korean Application No. 10-2017-0026969.
Nov. 12, 2019 Office Action Issued In Japanese Patent Application No. 2017-003616.
Apr. 17, 2019 Office Action issued in Taiwanese Application No. 106106753.
Jan. 13, 2020 Office Action issued in Taiwanese Application No. 106106753.

* cited by examiner (A)

(B)

(C)

101

111

BIOLOGICAL ELECTRODE AND MANUFACTURING METHOD THEREOF

This is a divisional of application Ser. No. 15/427,680 filed Feb. 8, 2017 and claims the benefit of Japanese Application Nos. 2016-040873 filed Mar. 3, 2016 and 2016-137840 filed Jul. 12, 2016. The entire disclosures of the prior applications are hereby incorporated by reference in their entirety.

TECHNICAL FIELD

The present invention relates to a biological electrode, which is in contact with living skin and can detect physical conditions such as a heart rate on the basis of electric signals from the skin, and a method for manufacturing thereof.

BACKGROUND ART

In recent years, wearable devices have been developed progressively with the spread of Internet of Things (IoT). Representative examples thereof include a watch and glasses that can be connected with internet. Wearable devices that can always monitor physical conditions are also necessary in a medical field and a sports field, and is expected to be a growth field in the future.

In the medical field, wearable devices have been investigated to monitor organic conditions by sensing a weak current such as an electrocardiogram measurement, which detects heart beats by electric signals. The electrocardiogram is measured by fitting a body with electrodes on which electro-conductive paste is applied, and this measurement is performed only once in a short period of time. On the other hand, the aim of development of the foregoing medical wearable device is to develop devices that monitor health conditions continuously for several weeks. Accordingly, biological electrodes used for a medical wearable device have to keep the electric conductivity unchanged and not to cause skin allergies even when being used for a long time. In addition to these, it is desirable that the biological electrode is light in weight and can be manufactured at low cost.

Medical wearable devices include a type in which the device is attached to a body and a type in which the device is incorporated into clothes. As the type in which the device is attached to a body, it has been proposed a biological electrode using water soluble gel containing water and electrolyte, which are materials of the foregoing electro-conductive paste (Patent Document 1). On the other hand, as the type in which the device is incorporated into clothes, it has been proposed a means to use cloth in which a conductive polymer such as poly-3,4-ethylenedioxythiophene-polystyrenesulfonate (PEDOT-PSS) or silver paste is incorporated into the fibers for electrodes (Patent Document 2).

When using the foregoing water soluble gel containing water and electrolyte, however, the electric conductivity is lost as the water is lost due to drying. The use of an electro-conductive polymer such as PEDOT-PSS also has a risk of skin allergies due to the strong acidity of the electro-conductive polymer.

As the electrode material, it has been investigated to use metal nanowire, carbon black, and carbon nanotube since they have excellent electric conductivity. The metal nanowire can conduct electricity in a small loading amount since the wires are brought into contact with each other in high probability. The metal nanowire, however, can cause skin allergies since they are thin material with sharp tips. The carbon nanotube also has a risk of biocompatibility when used alone by the same reason. The carbon black has irritativeness to skin when used alone, although the toxicity is lower than the carbon nanotube. As described above, the biocompatibility is sometimes worsened due to the shape and irritativeness of a material, even though the material itself does not cause an allergic reaction. Accordingly, it has been difficult to achieve both the electric conductivity and the biocompatibility.

As a means for solving these problems, it has been investigated to use electro-conductive metal particles as an electrode material. Among metals, noble metals such as gold, silver, and platinum, which have lowest ionization tendencies, are hard to cause skin allergies. Accordingly, it is possible to achieve both the electric conductivity and the biocompatibility by using these noble metal particles. When mixing these noble metal particles into a resin, however, electricity is not conducted unless the particles are brought into contact with each other in the resin, which is an insulator. In order to bring the particles into contact with each other, the noble metal particles have to be loaded in a volume ratio of 70% or more. As described above, when using metal particles, it is necessary to load a large amount of expensive noble metal particles, and accordingly, the production cost becomes very high and the weight increases, thereby making it impossible to achieve weight reduction, which is necessary for wearable devices.

PRIOR ART DOCUMENTS

Patent Documents

Patent Document 1: International Patent Laid-Open Publication No. WO 2013/039151
Patent Document 2: Japanese Unexamined Patent publication (Kokai) No. 2015-100673

SUMMARY OF INVENTION

Technical Problem

The present invention has been accomplished to solve the foregoing problems, and an object thereof is to provide a biological electrode that is superior in electric conductivity and biocompatibility, light in weight, and can be manufactured at low cost; as well as a method for manufacturing thereof.

Solution to Problem

To achieve the object, the present invention provides a biological electrode comprising an electro-conductive base material and a living body contact layer formed on the electro-conductive base material;
wherein the living body contact layer comprises a resin layer and particles dispersed in the resin layer, the particles being coated with gold, silver, or platinum, and a thickness of the resin layer is equal to or thinner than an average particle size of the particles.

Such a biological electrode can be a biological electrode that is superior in electric conductivity and biocompatibility, light in weight, and can be manufactured at low cost.

It is preferable that the average particle size of the particles be 1 μm or more and 1,000 μm or less, and the thickness of the resin layer be 0.5 μm or more and 1,000 μm or less.

When the particles have such an average particle size, and the resin layer has such a thickness, the biological electrode can be lighter while ensuring its sufficient electric conductivity, and the production cost can be reduced.

It is preferable that the ratio of the thickness of the resin layer to the average particle size of the particles be 0.5 or more and 1.0 or less.

Such a ratio of the thickness of the resin layer to the average particle size of the particles enables the resin layer to hold the particles sufficiently, and to effectively prevent lowering of the electric conductivity due to separation of particles.

It is preferable that the particles constitute 0.5% or more and 70% or less in a volume ratio on the basis of a total volume of the resin layer and the particles.

Such a volume ratio of the particles enables the biological electrode to be lighter while ensuring its sufficient electric conductivity, and to reduce the production cost.

The resin layer is preferably a cured product of a resin composition comprising at least one of a thermosetting resin and a photo-curable resin.

Such a resin layer can be formed easily, and is suitable for the inventive biological electrode thereby.

The resin layer is preferably a cured product of a resin composition comprising a silicon-containing resin having one or more moieties selected from a siloxane bond, an ester bond, an amide bond, an imide bond, an urethane bond, a thiourethane bond, and a thiol group.

Such a resin layer has good adhesion properties to an electro-conductive base material and particles as well as high water repellency and slight tendency to be hydrolyzed, which can make the biological electrode be less susceptible to perspiration.

The resin layer is preferably a cured product of a resin composition comprising one or more resins selected from a silicone resin, a silicon atom-containing polyacrylic resin, a silicon atom-containing polyamide resin, a silicon atom-containing polyimide resin, a silicon atom-containing polyurethane resin, and a silicon atom-containing polythiourethane resin.

Such a resin layer has good adhesion properties to an electro-conductive base material and particles as well as high water repellency and slight tendency to be hydrolyzed, which can make the biological electrode be less susceptible to perspiration.

The electro-conductive base material preferably comprises one or more species selected from gold, silver, silver chloride, platinum, aluminum, magnesium, tin, tungsten, iron, copper, nickel, titanium, stainless, and carbon.

Such an electro-conductive base material can be suitably used for the inventive biological electrode.

The particles are preferably spherical particles.

Such particles can conduct electricity from a living body more uniformly, and can further reduce stimuli to skin in fitting.

The particles are preferably resin particles coated with gold, silver, or platinum, the resin particles comprising one or more resins selected from polyacrylate, polyethylene, polypropylene, polystyrene, polydivinylbenzene, novolac, and polyurethane.

Such particles are lighter and lower in cost compared to particles entirely composed of gold, silver, or platinum. Accordingly, it is possible to make the biological electrode lighter, and to reduce the production cost.

It is preferable that the particles each have an electro-conductive metal layer comprising one or more electro-conductive metals selected from silver, aluminum, copper, nickel, tungsten, and tin in an interior of the particle.

Such particles can give electric conductivity by the electro-conductive metal layer in the particle even when the gold, silver, or platinum on the surface of the particles are thinned, thereby making it possible to further reduce the production cost while ensuring sufficient electric conductivity.

It is also preferable that the thickness of the resin layer be thinner than the average particle size of the particles, and the particles be exposed convexly from a surface of the resin layer.

When the particles are exposed convexly from the surface of the resin layer as described above, the contact area between the particles and a living body increases, and accordingly, it is possible to efficiently pick a weak current from a living body.

The particles are preferably disposed such that each of the particles is the only particle in a thickness direction of the resin layer.

Such arrangement of particles makes it possible to reduce the required amount of particles to a minimum while ensuring sufficient electric conductivity. Accordingly, the biological electrode can be lighter, and the production cost can be reduced.

The present invention also provides a method for manufacturing a biological electrode comprising: applying a composition comprising a resin and particles dispersed in the resin, the particles being coated with gold, silver, or platinum, onto an electro-conductive base material; and curing the resin under pressure; thereby forming a living body contact layer comprising the particles and a resin layer having a thickness equal to or thinner than an average particle size of the particles on the electro-conductive base material.

Such a manufacturing method can manufacture a biological electrode that is superior in electric conductivity and biocompatibility, and is light in weight at low cost.

It is preferable that the average particle size of the particles be 1 µm or more and 1,000 µm or less, and the resin layer be formed to have a thickness of 0.5 µm or more and 1,000 µm or less.

By using the particles having such an average particle size, and making the resin layer have such a thickness, it is possible to manufacture a biological electrode having a lighter weight while ensuring its sufficient electric conductivity, and to reduce the production cost.

It is preferable that the resin layer be formed to have a thickness with a ratio of the thickness to the average particle size of the particles being 0.5 or more and 1.0 or less.

Such a ratio of the thickness of the resin layer to the average particle size of the particles enables the resin layer to hold the particles sufficiently. Accordingly, it is possible to manufacture a biological electrode in which lowering of the electric conductivity due to separation of particles is effectively prevented.

It is preferable that the particles constitute 0.5% or more and 70% or less in a volume ratio on the basis of a total volume of the formed resin layer and the particles.

Such a volume ratio of the particles makes it possible to manufacture a biological electrode having a lighter weight while ensuring its sufficient conductivity, and to reduce the production cost.

It is preferable that the resin be at least one of a thermosetting resin and a photo-curable resin, and be cured by either or both of heat and light.

The resins and the methods for curing thereof make it possible to form the resin layer easily.

The resin is preferably a silicon-containing resin having one or more moieties selected from a siloxane bond, an ester bond, an amide bond, an imide bond, an urethane bond, a thiourethane bond, and a thiol group.

By using such a resin, it is possible to form a resin layer having good adhesion properties to an electro-conductive base material and particles as well as high water repellency, and being hard to be hydrolyzed. Accordingly it is possible to manufacture a biological electrode that is less susceptible to perspiration.

The resin is preferably one or more resins selected from a silicone resin, a silicon atom-containing polyacrylic resin, a silicon atom-containing polyamide resin, a silicon atom-containing polyimide resin, a silicon atom-containing polyurethane resin, and a silicon atom-containing polythiourethane resin.

By using such a resin, it is possible to form a resin layer having good adhesion properties to an electro-conductive base material and particles as well as high water repellency, and being hard to be hydrolyzed. Accordingly, it is possible to manufacture a biological electrode that is less susceptible to perspiration.

It is preferable that the electro-conductive base material comprise one or more species selected from gold, silver, silver chloride, platinum, aluminum, magnesium, tin, tungsten, iron, copper, nickel, titanium, stainless, and carbon.

Such an electro-conductive base material can be suitably used for the inventive method for manufacturing a biological electrode.

It is preferable that the particles be spherical particles.

By using such particles, it is possible to manufacture a biological electrode that can conduct electricity from a living body more uniformly, and can further reduce stimuli to skin in fitting.

It is preferable that the particles be resin particles coated with gold, silver, or platinum, the resin particles comprising one or more resins selected from polyacrylate, polyethylene, polypropylene, polystyrene, polydivinylbenzene, novolac, and polyurethane.

Such particles are lighter and lower in cost compared to particles entirely composed of gold, silver, or platinum. Accordingly, by using these particles, it is possible to produce a biological electrode having a lighter weight, and to reduce the production cost.

It is preferable that the particles each have an electro-conductive metal layer comprising one or more electro-conductive metals selected from silver, aluminum, copper, nickel, tungsten, and tin in an interior of the particle.

Such particles can give electric conductivity by the electro-conductive metal layer in the particle even when the gold, silver, or platinum on the surface of the particles are thinned. Accordingly, by using these particles, it is possible to further reduce the production cost while ensuring sufficient electric conductivity.

It is preferable that the resin layer be formed to have a thickness thinner than the average particle size of the particles, and the particles be exposed convexly from a surface of the resin layer.

When the particles are exposed convexly from the surface of the resin layer as described above, it is possible to increase the contact area between the particles and a living body, and to improve the efficiency to pick a weak current from a living body.

It is preferable that the particles be disposed such that each of the particles is the only particle in a thickness direction of the resin layer.

Such arrangement of particles makes it possible to suppress the required amount of particles to a minimum while ensuring sufficient electric conductivity. Accordingly, it is possible to manufacture a biological electrode having a lighter weight, and to reduce the production cost.

Advantageous Effects of Invention

As described above, the inventive biological electrode can efficiently conduct electric signals from skin to a device (i.e., having excellent electric conductivity), is free from the risk of causing allergies even when it is worn on skin for a long time (i.e., having excellent biocompatibility), can reduce the required amount of particles to a minimum, which makes the biological electrode be lighter, and can be manufactured at low cost. By adjusting the composition and the thickness of the resin layer appropriately, it is possible to prevent lowering of the electric conductivity due to wetting by perspiration from a living body, drying, or separation of the particles; and to add elasticity and tackiness to a living body. Accordingly, such an inventive biological electrode is particularly suitable for a biological electrode used for a medical wearable device. Moreover, the inventive method for manufacturing a biological electrode can manufacture such a biological electrode easily at low cost.

DESCRIPTION OF EMBODIMENTS

As described above, when a biological electrode uses particles made of noble metal such as gold, silver, and platinum, the biocompatibility becomes excellent. In order to obtain sufficient electric conductivity, however, it is necessary to load a large amount of noble metal particles so as to bring the particles in contact with each other. The use of a large amount of expensive noble metal materials increases the production cost, and the containing of a large amount of particles causes an increase of the weight.

The present inventors have diligently investigated to solve the foregoing subject. As a result, the inventors have found that by using particles coated with gold, silver, or platinum, which is hard to cause skin allergies, as the electro-conductive particles loaded into the living body contact layer, and making the thickness of the resin layer equal to or thinner than the average particle size of the particles, it is possible to achieve both the electric conductivity and the biocompatibility, and to suppress the required amount of particle, which can bring lighter weight and reduction of the production cost; thereby completing the present invention.

That is, the present invention is a biological electrode comprising an electro-conductive base material and a living body contact layer formed on the electro-conductive base material;

wherein the living body contact layer comprises a resin layer and particles dispersed in the resin layer, the particles being coated with gold, silver, or platinum, and a thickness of the resin layer is equal to or thinner than an average particle size of the particles.

Hereinafter, the inventive biological electrode will be specifically described with reference to the FIGS., but the present invention is not limited thereto.

<Biological Electrode>

Figure 1:
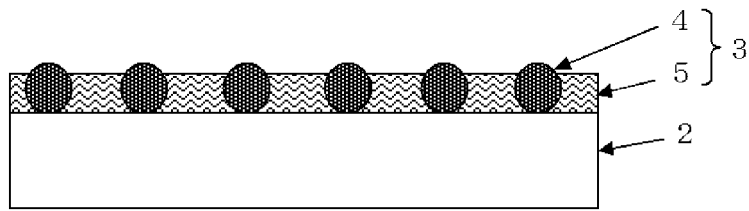
FIG. 1 is a schematic sectional view showing an example of the inventive biological electrode.

FIG. 1 is a schematic sectional view showing an example of the inventive biological electrode. The biological electrode 1 of FIG. 1 has the electro-conductive base material 2 and the living body contact layer 3 formed on the electro-conductive base material 2. The living body contact layer 3 comprises the resin layer 5 and the particles 4, the surface of which are coated with gold, silver, or platinum, dispersed in the resin layer 5. The thickness of the resin layer 5 is equal to or thinner than the average particle size of the particles 4. That is, a side of the surface of each particle 4 is exposed on the surface of the side that is in contact with a living body (i.e., the particles 4 are exposed convexly from the surface of the resin layer 5), and the opposite side of the surface of each particle 4 is in contact with the electro-conductive base material 2. Moreover, the particles 4 are disposed such that each of the particles 4 is the only particle in a thickness direction of the resin layer 5, without stacking with each other.

Figure 2:
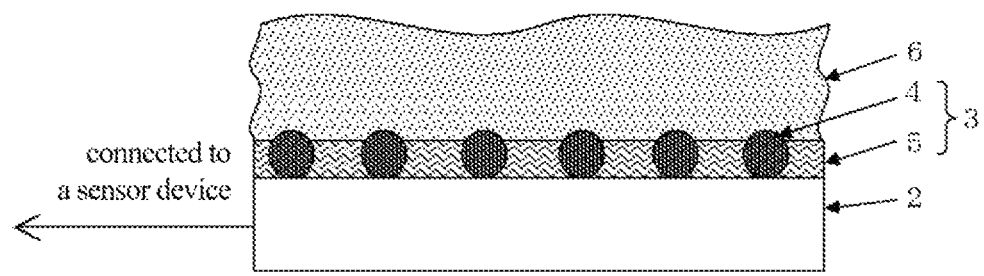
FIG. 2 is a schematic sectional view showing an example of the inventive biological electrode worn on a living body.

When using the biological electrode 1 of FIG. 1, electric signals are picked from a living body 6 through particles 4 while bringing the living body contact layer 3 (i.e., particles 4 and the resin layer 5) with the living body 6, and then conducted to a sensor device (not shown) through the electro-conductive base material 2, as shown in FIG. 2. In the inventive biological electrode, the thickness of the resin layer is equal to or thinner than the average particle size of the particles, and accordingly, the amount of particles required for conducting can be suppressed to a minimum. Moreover, since the particles are exposed convexly from the surface of the resin layer, the contact area between the particles and a living body is large, which brings excellent electric conductivity.

Figure 4:
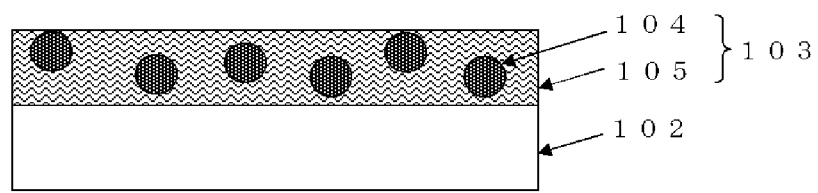
FIG. 4 is a schematic sectional view showing an example of a biological electrode in which the thickness of the resin layer is thicker than the average particle size of the particles.

Herein, FIG. 4 shows an example of a biological electrode in which the thickness of the resin layer is thicker than the average particle size of the particles. In the biological electrode 101 of FIG. 4, although the living body contact layer 103 comprising the particles 104 and the resin layer 105 is formed on the electro-conductive base material 102, the thickness of the resin layer 105 is thicker than the average particle size of the particles 104. That is, the particles 104 are not in contact with the electro-conductive base material 102, and are not exposed on the surface of the side that is in contact with a living body. Moreover, the particles 104 are not in contact with each other. Accordingly, electricity from a living body does not conducted to the electro-conductive base material 102.

Figure 5:
FIG. 5 is a schematic sectional view showing another example of the biological electrode in which the thickness of the resin layer is thicker than the average particle size of the particles.

FIG. 5 shows another example of the biological electrode in which the thickness of the resin layer is thicker than the average particle size of the particles. In the biological electrode 111 of FIG. 5, the living body contact layer 103 comprising a large amount of particles 104 and the resin layer 105 on the electro-conductive base material 102. Accordingly, electricity can be conducted as such even when the thickness of the resin layer 105 is thicker than the average particle size of the particles 104. As described above, however, when loading such a large amount of particles, it is not possible to conduct electricity unless the ratio of the particles is at least 70% on the basis of the volume of the living body contact layer. That is, this case needs a large amount of expensive noble metal particles, and accordingly, the production cost increases, and weight reduction cannot be achieved.

Hereinafter, each component composing the inventive biological electrode will be specifically described.

[Electro-Conductive Base Material]

The inventive biological electrode comprises an electro-conductive base material. This electro-conductive base material is usually connected electrically with a sensor device and so on, and conduct electrical signals picked from a living body through the particles to the sensor device, etc.

The electro-conductive base material is not particularly limited as long as it is electro-conductive. However, it is preferable to comprise one or more species selected from gold, silver, silver chloride, platinum, aluminum, magnesium, tin, tungsten, iron, copper, nickel, titanium, stainless, and carbon, for example.

The electro-conductive base material is not particularly limited, and may be a hard electro-conductive substrate, an electro-conductive film having flexibility, and an electro-conductive cloth that is a hybrid of the foregoing electro-conductive material and fiber, and can be appropriately selected based on the use of the biological electrode. Particularly, when the inventive biological electrode is attached to skin or is brought into contact with skin as a part of a cloth, it has to be flexible. Accordingly, it is desirable that the living body contact layer be formed onto the flexible electro-conductive film or on the electro-conductive cloth.

[Living Body Contact Layer]

The inventive biological electrode comprises a living body contact layer formed on the electro-conductive base material. This living body contact layer is a part to be in contact with a living body actually when using the biological electrode. This living body contact layer comprises a resin layer and particles dispersed in the resin layer, the surfaces of the particles being coated with gold, silver, or platinum.

(Particles)

In the inventive biological electrode, the particles composing the living body contact layer is electron-conductive particles, the surface of which is coated with gold, silver, or platinum, and is intended to pick weak electrical signals from a living body and to conduct this to the foregoing electro-conductive base material.

The particles are preferably resin particles coated with gold, silver, or platinum, the resin particles comprising one or more resins selected from polyacrylate, polyethylene, polypropylene, polystyrene, polydivinylbenzene, novolac, and polyurethane. Such particles are lighter and lower in cost compared to particles entirely composed of gold, silver, or platinum. Accordingly, it is possible to make the biological electrode lighter, and to reduce the production cost.

The outmost surface of the particle, being in contact with skin, have to be gold, silver, or platinum, which is a noble metal without causing skin allergies. In the interior of the particle, however, an electro-conductive metal layer comprising one or more electro-conductive metals selected from silver, aluminum, copper, tungsten, tin, etc. may be contained. It is effective to make this layer as thin as possible for reducing the cost since gold, silver, and platinum are expensive. If the layer of gold, silver, or platinum is too thin, however, the electric conductivity is lowered. Accordingly, it is effective to ensure the necessary electric conductivity by forming an electro-conductive metal layer comprising metal selected from aluminum, copper, nickel, tungsten, tin, etc., which are low cost, in the interior of the particle. Incidentally, the thickness of the gold, silver, or platinum layer on the particle surface is not particularly limited. However, it is preferably set to about several nm since the production cost can be reduced by thinning this layer as described above.

The average particle size of the particles, the surface of which being coated with gold, silver, or platinum, is preferably 1 μm or more and 1,000 μm or less, more preferably 2 μm or more and 800 μm or less, and further preferably 3 μm or more and 600 μm or less. When the average particle size of the particles is 1 μm or more, it is not difficult to form the resin layer, which have to be formed with the thickness being equal to or thinner than an average particle size of the particles. When the average particle size of the particles is 1,000 μm or less, the particles can be held without difficulty due to large particles, and the biological electrode is free from a risk of increasing the weight too much.

Incidentally, it is preferable that the variation of the particle size be as small as possible. More specifically, the standard deviation of the particle size when measuring 10 pieces of the particles is preferably 10% or less on the basis of the average particle size, and is more preferably, 5% or less on the basis of the average particle size. As the variation of the particle size is smaller, the exposure ratio of the particles exposed from the surface of the resin layer (i.e., the contact area between the particles and a living body) becomes more uniform, and the electric conductivity from a living body becomes more uniform thereby.

The particles are preferably spherical particles. The spherical particles makes it possible to conduct electricity from a living body more uniformly. It is also possible to reduce the stimuli to skin in wearing the biological electrode. Although the shape of the particle is most preferably a spherical shape, but can be an ellipse, a quadrilateral, a cone, and the other indeterminate forms.

As the spherical particle in which the surface of a resin particle is coated with gold, silver, or platinum, it is also possible to use the ones previously used as an electro-conductive adhesive and a spacer for conducting Liquid Crystal Display (LCD) and its driving circuit. Illustrative examples of such a particle include the ones described in Japanese Unexamined Patent publication (Kokai) No. H11-209714, Japanese Unexamined Patent publication (Kokai) No. 2006-156068, Japanese Unexamined Patent publication (Kokai) No. 2011-204530, and Japanese Unexamined Patent publication (Kokai) No. 2015-109268.

(Resin Layer)

In the inventive biological electrode, the foregoing particles are dispersed in the resin layer composing the living body contact layer. The resin layer is a layer to prevent separation of these particles from the living body contact layer, and to hold the particles. The resin layer is preferably a cured product of a resin composition comprising either or both of a thermosetting resin and a photo-curable resin.

In the inventive biological electrode, the resin layer preferably has a high adhesion properties to the foregoing particles, the surface of which is coated with gold, silver, or platinum, in order to prevent lowering of the electric conductivity due to separation of the particles from the resin layer. In the inventive biological electrode, the resin layer preferably has a high adhesion properties to the electro-conductive base material too in order to prevent peeling of the living body contact layer from the electro-conductive base material. In order to improve the adhesion properties of the resin layer to the electro-conductive base material and the particles coated with gold, silver, or platinum, it is effective to use a resin with high polarity. Illustrative examples of such a resin include a resin having one or more moieties selected from an ester bond, an amide bond, an imide bond, an urethane bond, a thiourethane bond, and a thiol group; as well as a polyacrylic resin, a polyamide resin, a polyimide resin, a polyurethane resin, and a polythiourethane resin. On the other hand, the resin layer is brought into contact with a living body, and is liable to be affected by perspiration from a living body thereby. Accordingly, in the inventive biological electrode, the resin layer is preferably highly water repellent and hard to be hydrolyzed. In order to make the resin layer be highly water repellent and hard to be hydrolyzed, the use of a silicon-containing resin is effective.

Accordingly, in the inventive biological electrode, it is preferable that the resin layer be a cured product of a resin composition comprising a silicon atom-containing resin having one or more moieties selected from a siloxane bond, an ester bond, an amide bond, an imide bond, an urethane bond, a thiourethane bond, and a thiol group.

The resin layer is also preferable to be a cured product of a resin composition comprising one or more resins selected from a silicone resin, a silicon atom-containing polyacrylic resin, a silicon atom-containing polyamide resin, a silicon atom-containing polyimide resin, a silicon atom-containing polyurethane resin, and a silicon atom-containing polythiourethane resin.

Such a resin layer has good adhesion properties to the electro-conductive base material and the particles as well as high water repellency and slight tendency to be hydrolyzed, which can make the biological electrode be less susceptible to perspiration. That is, it is possible to achieve both water repellency and adhesion properties.

As described above, the resin layer is preferably a cured product of a resin composition. Curing improves the adhesion properties of the resin layer to both of the particles and the electro-conductive base material. The curing means is not particularly limited, and general means can be used. For example, it is possible to use crosslinking reaction by either or both of heat and light, an acid catalyst, or a base catalyst. The crosslinking reaction can be performed by appropriately selecting a crosslinking agent described in "Kakyou han-nou handbook (handbook of crosslinking reaction)", Yasuharu Nakamura, Maruzen shuppan (2013), part 2, 51-371.

In manufacturing the inventive biological electrode, the composition comprising the particles and the resin are applied onto the electro-conductive base material, and subjected to contact bonding and stretching with a mold, for example, as will be described later. Accordingly, the resin before curing preferably has lower viscosity. Since the curing is carried out while pressing the material, the composition is preferably solvent free. The solvent free composition can be cured stably without a risk of sudden evaporation of solvent under pressure in the curing. By the same reason, it is preferable to select materials with lower vapor pressure as the resin and the crosslinking agent.

The silicon atom-containing polyacrylic resin includes a polymer that has a silicone main chain and a polymer that has a silicon atom(s) on the side chain. Each of them can be suitably used. As the polymer that has a silicone main chain, silsesquioxane or siloxane having a (meth)acrylpropyl group and so on can be used. In this case, an addition of a photoradical generator allows the (meth)acryl moiety to polymerize to cure.

When the side chain of the silicone contains a double bond(s) such as a vinyl group and an allyl group, photo-crosslinking can be performed by adding a thiol type crosslinking agent. It is to be noted that the thiol coordinates to gold. Accordingly, when using particles coated with gold, an addition of thiol gives an effect to improve the adhesiveness between the particles and the resin layer. In this case, the silicone does not necessarily have an ester bond, an amide bond, an imide bond, an urethane bond, and a thiourethane bond.

Illustrative examples of the suitable silicon atom-containing polyamide resin include polyamide silicone resins described in Japanese Unexamined Patent publication (Kokai) No. 2011-079946 and U.S. Pat. No. 5,981,680, for example. Such a polyamide silicone resin can be synthesized by combining a silicone or non-silicone compound having amino groups at the both terminals and a non-silicone or silicone compound having carboxy groups at the both terminals. When the silicone has a (meth)acrylpropyl group(s) at the side chain, it can be cured by photoradical crosslinking. When the silicone has a vinyl group(s) and an SiH group(s) (silicon atom-containing hydrogen atom), it can be crosslinked through an addition reaction by a platinum catalyst.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate, and to perform photoradical crosslinking of the (meth)acrylate moiety.

Illustrative examples of the suitable silicon atom-containing polyimide resin include polyimide silicone resins described in Japanese Unexamined Patent publication (Kokai) No. 2002-332305, for example. Although polyimide resins have very high viscosity, it can be changed to have low viscosity by blending a (meth)acrylic monomer as a solvent and a crosslinking agent.

Illustrative examples of the silicon atom-containing polyurethane resin include polyurethane silicone resins. These polyurethane silicone resins can be crosslinked through urethane bond by blending a compound having isocyanate groups at the both terminals and a compound having hydroxy groups at the terminal, and heating thereof. In this case, a silicon atom(s) (siloxane bond) have to be contained in either or both of the compound having isocyanate groups at the both terminals and the compound having hydroxy groups at the terminal. Alternatively, an urethane (meth)acrylate monomer and polysiloxane can be blended and photo-crosslinked as described in Japanese Unexamined Patent publication (Kokai) No. 2005-320418. It is also possible to crosslink a polymer having both of a siloxane bond(s) and an urethane bond(s), with the terminal having a (meth)acrylate group(s).

The silicon atom-containing polythiourethane resin can be obtained by reacting a compound having a thiol group(s) and a compound having an isocyanate group(s), and either of them have to contain a silicon atom(s). It can also be cured if (meth)acrylate groups are contained at the terminals, curing can also be performed.

To the composition for forming the resin layer, it is also possible to blend a non-silicon-containing resin(s) having an ester bond(s), an amide bond(s), an imide bond(s), an urethane bond(s), a thiourethane bond(s), and/or a thiol group(s). It is preferable to blend the non-silicon-containing resin(s) having an ester bond(s), an amide bond(s), an imide bond(s), an urethane bond(s), a thiourethane bond(s), and/or a thiol group(s) in an amount of 10 to 4,000 parts by mass on the basis of 100 parts by mass of the silicon-containing resin.

The curing is preferably performed by using a resin having (meth)acrylate terminals or adding a crosslinking agent having a terminal(s) of (meth)acrylate or a thiol group(s), together with adding a photoradical generator, which generates a radical by light, or thermal radical generator, which generates a radical by heat decomposition.

Illustrative examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yle)-4,6-bis(trichloroethyl)-1,3,5-triazine, 2-benzyl-2-(dimethylamino)-4'-morpholinobutylophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl) phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone. The loading amount of the photoradical generator is preferably in a range of 0.1 to 50 parts by mass on the basis of 100 parts by mass of the resin.

The curing can also be performed by adding a radical generator of a heat decomposition type. Illustrative examples of the thermal radical generator include 2,2'-azobis(isobutyronitrile), 2,2'-azobis(2,4-dimethylvaleronitrile), 2,2'-azobis(2-methylbutylonitrile), 4,4'-azobis(4-cyanovaleric acid), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(2-methylbutylonitrile), 2,2'-azobis(cyclohexane-1-carbonitrile), 1[(1-cyano-1-methylethyl)azo]formamide, 2,2'-azobis[2-methyl-N-(2-hydroxyethyl) propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dimethyl-2,2'-azobis(2-methylpropionate), and dicumyl peroxide.

To the composition for forming the resin layer, an adhesion improving agent may be added in order to improve the adhesion property of the resin layer and the particles. Illustrative examples of such an adhesion improving agent include silane coupling agents having a thiol group, a hydroxy group, a carboxy group, an amide group, and an urethane group.

Since the inventive biological electrode is used by being attached to a living body (e.g., skin), the composition for forming the resin layer may contain a tackifier in order to add tackiness to a living body. Illustrative examples of such a tackifier include a silicone resin, as well as non-crosslinkable siloxane, non-crosslinkable poly(meth)acrylate, and non-crosslinkable polyether.

It is to be noted that the thickness of the resin layer is preferably 0.5 µm or more and 1,000 µm or less, more preferably 1 μm or more and 800 μm or less, further preferably 2 μm or more and 600 μm or less.

The thickness of the resin layer is preferably in the ratio to the average particle size of the particles being 0.5 or more and 1.0 or less. In such a ratio, the resin layer can hold the particles sufficiently, and can effectively prevent lowering of the electric conductivity due to separation of the particles thereby.

In the inventive biological electrode, it is preferable that the thickness of the resin layer be thinner than the average particle size of the particles, and the particles be exposed convexly from the surface of the resin layer. When the particles are exposed convexly from the surface of the resin layer as described above, the contact area between the particles and a living body increases, and weak current from a living body can be efficiently picked thereby.

In the inventive biological electrode, it is also preferable that the particles constitute 0.5% or more and 70% or less in a volume ratio on the basis of a total volume of the resin layer and the particles (i.e., the volume of the living body contact layer). Such a volume ratio of the particles allows the biological electrode to be lighter in weight while ensuring sufficient electric conductivity, and to reduce the production cost.

To the composition for forming the living body contact layer of the inventive biological electrode, carbon type electro-conductive material can also be added in addition to the foregoing particles, the surface of which is coated with gold, silver, or platinum. Illustrative examples of the carbon type electro-conductive material include carbon black, acetylene black, ketjen black, and carbon nanotube. Any kinds of carbon nanotube can be used including single-wall nanotube, double-wall nanotube, and multi-wall nanotube having more layers. When the carbon type electro-conductive materials are exist between the particles coated with gold, silver, or platinum, electricity also conducts through the carbon type electro-conductive materials, and the living body contact layer shows better electric conductivity thereby. The combination of the particles, the surface of which is coated with gold, silver, or platinum, and the carbon type electro-conductive materials can give high electric conductivity while the addition amounts are smaller than in each case of adding a single electro-conductive material. The loading amount of the carbon type electro-conductive material is preferably in a range of 0.1 to 50 parts by mass on the basis of 100 parts by mass of the resin.

In the inventive biological electrode, the particles are preferably disposed such that each of the particles is the only particle in the thickness direction of the resin layer. Such an arrangement of the particles can suppress the required amount of particles to a minimum while ensuring sufficient electric conductivity, which can make the biological electrode lighter, and can reduce the production cost.

In the inventive biological electrode, it is also possible to separately provide a tacky film on the living body contact layer in order to prevent peeling off of the biological electrode from a living body during the use as in the previous biological electrodes (e.g., the biological electrode described in Japanese Unexamined Patent publication (Kokai) No. 2004-033468). The tacky film may be formed by using tackiness agent of an acrylic type, an urethane type, a silicone type, etc., when it is formed. Particularly, the silicone type is suitable since it has high transparency of oxygen and water, high water repellency, and low stimuli to a skin. It is to be noted that the inventive biological electrode does not necessarily require the foregoing tacky film since it is possible to prevent the peeling off from a living body by adding the tackifier to the composition for forming the resin layer or using a resin having good tackiness to a living body as described above.

When the inventive biological electrode is used as a wearable device, the components including the wiring between the biological electrode and a sensor device are not particularly limited. For example, it is possible to apply the ones described in Japanese Unexamined Patent publication (Kokai) No. 2004-033468.

As described above, the inventive biological electrode can conduct electric signals from skin to a device (i.e., having excellent electric conductivity), is free from the risk of causing allergies even when it is worn on skin for a long time (i.e., having excellent biocompatibility), can suppress the required amount of particles to a minimum, which makes the biological electrode lighter, and can be manufactured at low cost. By adjusting the composition and the thickness of the resin layer appropriately, it is possible to prevent lowering of the electric conductivity due to wetting by perspiration from a living body, drying, or separation of the particles; and to add elasticity and tackiness to a living body. Accordingly, such an inventive biological electrode is particularly suitable for a biological electrode used for a medical wearable device.

<Method for Manufacturing Biological Electrode>

The present invention also provides a method for manufacturing a biological electrode comprising: applying a composition comprising a resin and particles dispersed in the resin, the particles being coated with gold, silver, or platinum, onto an electro-conductive base material; and curing the resin under pressure; thereby forming a living body contact layer comprising the particles and a resin layer having a thickness equal to or thinner than the average particle size of the particles on the electro-conductive base material.

Hereinafter, the inventive method for manufacturing a biological electrode will be specifically described with reference to the FIGS., but the inventive method for manufacturing a biological electrode is not limited thereto.

Figure 3:
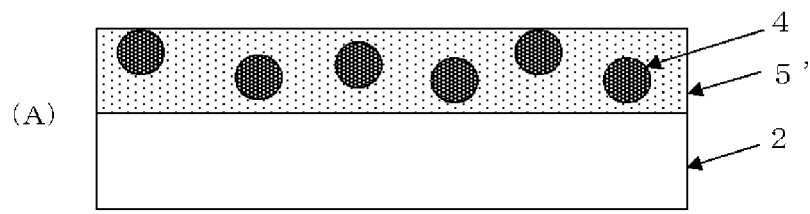
FIG. 3 is an explanatory drawing showing an example of the inventive method for manufacturing a biological electrode.
Figure 3:
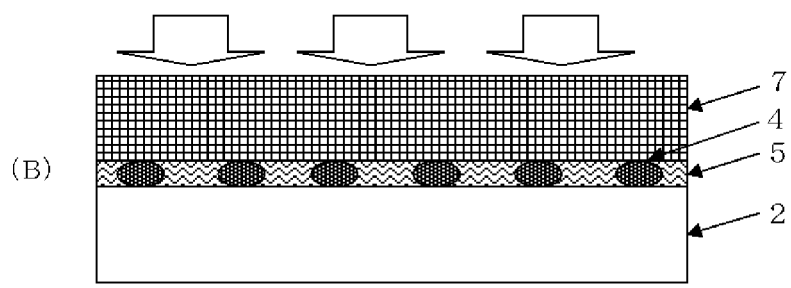
Figure 3:
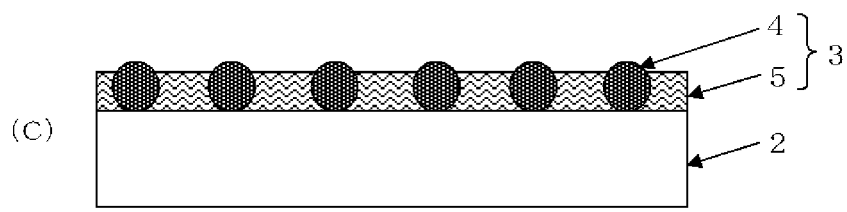

FIG. 3 is an explanatory drawing showing an example of the inventive method for manufacturing a biological electrode. In the manufacturing method of FIG. 3, a composition comprising the resin (the resin layer material 5') and the particles 4 dispersed in the resin, the particles 4 being coated with gold, silver, or platinum, is applied onto the electro-conductive base material 2 at first as shown in FIG. 3(A). Then, the resin is subjected to crosslinking and curing while pressing with the mold 7 as shown in FIG. 3(B) to form the resin layer 5. In this case, although the particles 4 deform by pressing, the shapes of the particles 4 return to their original shapes by removing the mold 7 after curing, thereby making it possible to form the cured resin layer 5 to have a thickness equal to or thinner than the average particle size of the particles 4 as shown in FIG. 3(C). These procedures make it possible to manufacture a biological electrode in which the living body contact layer 3 is formed on the conductive base material 2, with the living body contact layer 3 comprising the resin layer 5 and particles 4 dispersed in the resin layer 5, as shown in FIG. 3(C).

It is to be noted that in the inventive method for manufacturing a biological electrode, it is possible to use the same ones described above as the conductive base material, the particles coated with gold, silver, or platinum, the resin, the thickness of the resin layer and the volume ratio of the particles in the biological electrode to be manufactured, etc.

The method for applying the composition onto the electro-conductive base material is not particularly limited. It is suitable to use a method such as dip coating, spray coating, spin coating, roll coating, flow coating, and doctor coating.

The method for curing the resin is not particularly limited, and can be appropriately selected based on a kind of resin used for the resin layer. However, the resin is preferably cured by either or both of heat and light, for example. The foregoing composition can also be cured by adding a catalyst to generate acid or base, which causes a crosslinking reaction.

In case of heating, the temperature is not particularly limited, and may be appropriately selected based on a kind of resin used for the resin layer. However, it is preferable to be about 50 to 250° C. for example.

When curing is performed by photo-polymerization reaction (e.g., photo-crosslinking by radicals), the mold used for pressing is preferably a transparent material with high optical transmission. Incidentally, in curing by light, heating is not essential.

When the heating and light irradiation are combined, it is possible to perform the heating and the light irradiation simultaneously, to perform the heating after the light irradiation, or to perform the light irradiation after the heating.

In curing, the resin have to be cured under pressure (press curing). The pressure in the press curing is not particularly limited, but is preferably 0.01 to 100 kg/cm², for example. It is possible to adjust the thickness of the resin layer and the heights of the convexly exposed particles based on the foregoing deform extent of the particles. The thickness of the resin layer can also be adjusted by the distance between the mold 7 and the electro-conductive base material 2 in the pressing. It is also possible to heat while pressing in order to improve the fluidity of the resin during pressing and to accelerate the crosslinking reaction.

As described above, the inventive method for manufacturing a biological electrode can easily manufacture the inventive biological electrode that is superior in electric conductivity and biocompatibility, and is light in weight at low cost.

EXAMPLES

Hereinafter, the present invention will be specifically described with reference to Examples and Comparative Examples, but the present invention is not limited thereto. Incidentally, the weight average molecular weight (Mw) represents a weight average molecular weight in terms of polystyrene determined by gel permeation chromatography (GPC).

As the particles coated with gold, silver, or platinum, Micropearl AU (manufactured by SEKISUI CHEMICAL CO. LTD.), which are spherical particles coated with gold (Au-coated particle) with the average particle sizes of 10 μm, 20 μm, and 40 μm; and Ag-coat powders (manufactured by Mitsubishi Materials Electronic Chemicals Co., Ltd.), which are spherical particles coated with silver (Ag-coated particle) with the average particle size of 30 μm, were used.

The following are Polymers 1 to 6 each blended to a composition for forming a living body contact layer as a resin.

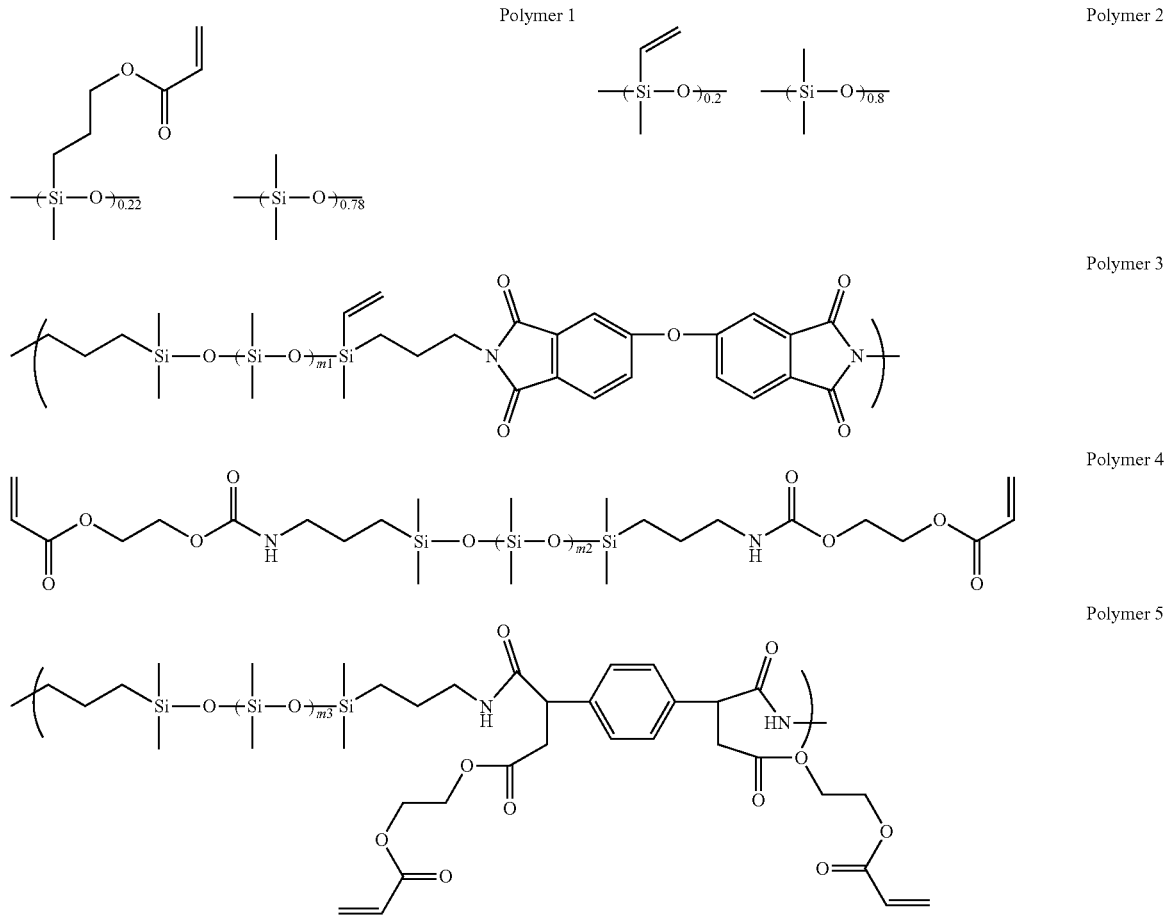

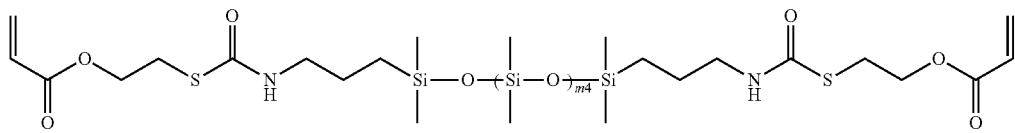

Polymer 6

(Herein, m1, m2, m3, and m4 each represents an integer of 8 to 12.)

Polymer 1: silicone resin
 Molecular weight (Mw)=5,200
 Dispersity (Mw/Mn)=2.22
Polymer 2: silicone resin
 Molecular weight (Mw)=7,200
 Dispersity (Mw/Mn)=2.85
Polymer 3: silicone polyimide resin
 Molecular weight (Mw)=6,500
 Dispersity (Mw/Mn)=3.2
Polymer 4: silicone urethane resin
 Molecular weight (Mw)=1,500
 Dispersity (Mw/Mn)=1.8
Polymer 5: silicone imide resin
 Molecular weight (Mw)=5,900
 Dispersity (Mw/Mn)=3.3
Polymer 6: silicone thiourethane resin
 Molecular weight (Mw)=1,600
 Dispersity (Mw/Mn)=1.8

The following are Urethane acrylates 1 to 3 each blended to a composition for forming a living body contact layer as a non-silicon-containing resin for blending.

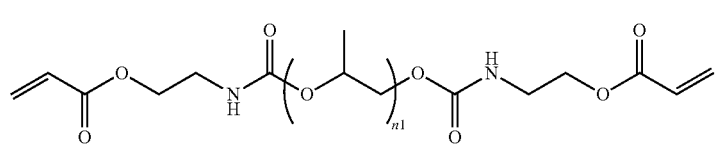

Urethane acrylate 1

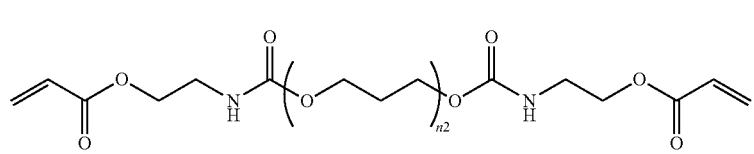

Urethane acrylate 2

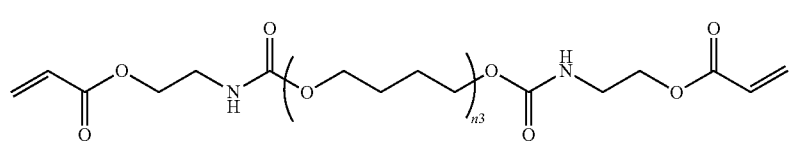

Urethane acrylate 3

(Herein, n1 was 50 on average, n2 was 60 on average, and n3 was 70 on average.)

The following are Crosslinking agents 1 to 4 each blended to a composition for forming a living body contact layer as an additive.

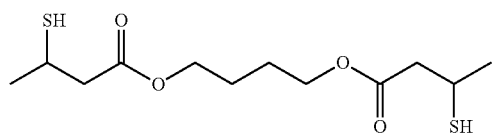

Crosslinking agent 1

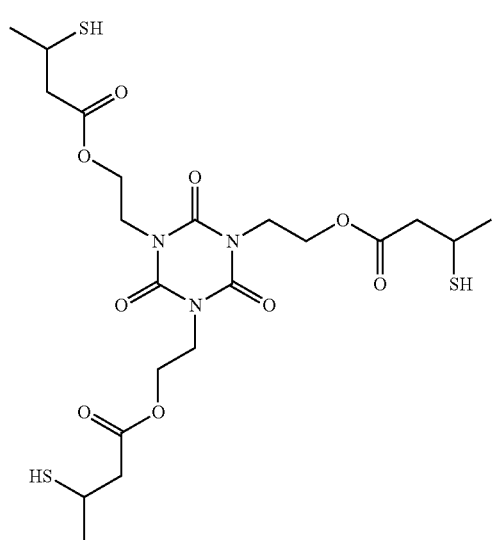

Crosslinking agent 2

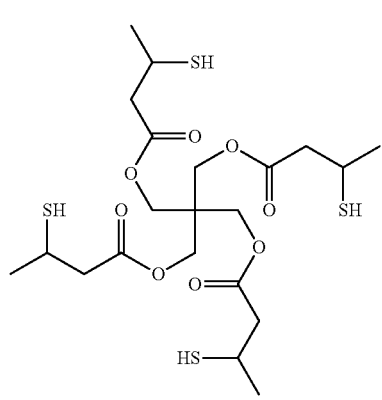

Crosslinking agent 3

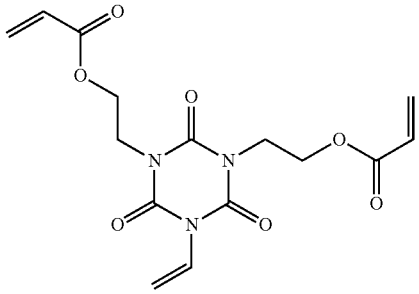

Crosslinking agent 4

The following are Adhesion improving agents 1 and 2 each blended to a composition for forming a living body contact layer as an additive.

Adhesion improving agent 1: 3-ureidopropyltrialkoxysilane

Adhesion improving agent 2: 3-mercaptopropyltrimethoxysilane

The following are Photoradical generator 1 and Thermal radical generator 1 each blended to a composition for forming a living body contact layer as an additive. Photoradical generator 1: dimethoxyphenylacetophenone Thermal radical generator 1: dimethyl-2,2'-azobis(2-methylpropionate)

Examples 1 to 12, Comparative Examples 1 and 2

The particles, the polymer(s), and the additives (crosslinking agent, adhesion improving agent, and radical generator) were blended in each formulation described in Table 1 to prepare solutions of composition for forming a living body contact layer. A copper plate with a thickness of 0.5 mm plated with nickel as an electro-conductive base material was placed on a hot plate. Onto this copper plate, each solution of composition for forming a living body contact layer was dispensed. This was pressed by using a quartz substrate on the side of the solution of composition for forming a living body contact layer with a thin film of tetrafluoroethylene sheet being inserted therebetween. Each pressing was carried out under a pressure described in Table 1, while irradiating light and/or heating (each temperature is described in Table 1), and the resin was crosslinked and cured thereby to produce a biological electrode. In Examples 1 to 8 and Comparative Examples 1 and 2, light was irradiated with an exposure value of 2 J/cm$^2$ using a halogen lamp, and the substrate was heated in some cases. In Examples 9 to 12, the substrate was heated without irradiating light.

Each of the biological electrodes thus produced was cut with a cutter, the cross-section was observed under an electron microscope to measure the thickness of the resin layer. These results are shown in Table 1.

The electric conductivity of the produced biological electrode was evaluated by measuring the resistivity using a method in conformity to JIS K 6271 with a Voltage/Current Generator 6241A manufactured by ADC COROPORATION. The results are shown in Table 1.

TABLE 1

| | Particle & Average particle size (μm) (parts by mass) | Polymer (parts by mass) | Additives (parts by mass) | Pressure (kg/cm²) | Temperature (° C.) | Thickness of resin layer (μm) | Electric resistance (Ω) |
|---|---|---|---|---|---|---|---|
| Example 1 | Au-coated particle 40 (25) | Polymer 1 (100) | Crosslinking agent 4 (5) Adhesion improving agent 1 (1) Photoradical generator 1 (2) | 3 | 23 | 32.0 | 7.0 |
| Example 2 | Au-coated particle 100 (30) | Polymer 2 (100) | Crosslinking agent 1 (10) Adhesion improving agent 2 (1) Photoradical generator 1 (2) | 3 | 23 | 90 | 15.3 |
| Example 3 | Au-coated particle 100 (20) | Polymer 2 (100) | Crosslinking agent 2 (5) Photoradical generator 1 (2) | 3 | 23 | 90 | 13.3 |
| Example 4 | Au-coated particle 10 (24) | Polymer 2 (100) | Crosslinking agent 3 (7) Photoradical generator 1 (2) | 3 | 23 | 9.0 | 16.3 |
| Example 5 | Au-coated particle 40 (37) | Polymer 3 (100) | Crosslinking agent 1 (10) Crosslinking agent 4 (5) Photoradical generator 1 (2) | 5 | 60 | 36.0 | 4.3 |
| Example 6 | Au-coated particle 20 (28) | Polymer 4 (100) | Photoradical generator 1 (2) | 3 | 60 | 18.2 | 8.7 |
| Example 7 | Au-coated particle 100 (20) | Polymer 5 (60) Polymer 1 (40) | Photoradical generator 1 (2) | 3 | 60 | 90 | 19.1 |
| Example 8 | Au-coated particle 10 (25) | Polymer 6 (100) | Crosslinking agent 3 (7) Photoradical generator 1 (2) | 3 | 60 | 9.0 | 46.8 |
| Example 9 | Ag-coated particle 30 (15) | Polymer 4 (20) Urethane acrylate 1 (80) | Thermal radical generator 1 (2) | 1.5 | 110 | 28.0 | 16.5 |
| Example 10 | Au-coated particle 100 (15) | Polymer 4 (20) Urethane acrylate 1 (80) | Thermal radical generator 1 (2) | 1.5 | 110 | 95.0 | 8.0 |
| Example 11 | Au-coated particle 100 (15) | Polymer 4 (20) Urethane acrylate 2 (80) | Thermal radical generator 1 (2) | 1.5 | 110 | 92.0 | 6.4 |
| Example 12 | Au-coated particle 100 (15) | Polymer 4 (40) Urethane acrylate 3 (60) | Thermal radical generator 1 (2) | 1.5 | 110 | 89.0 | 11.3 |
| Comparative Example 1 | Au-coated particle 10 (15) | Polymer 1 (100) | Crosslinking agent 4 (5) Adhesion improving agent 1 (1) Photoradical generator 1 (2) | 0 | 23 | 70 | $6.5 \times 10^3$ |
| Comparative Example 2 | Au-coated particle 10 (80) | Polymer 1 (20) | Crosslinking agent 4 (5) Adhesion improving agent 1 (1) Photoradical generator 1 (2) | 0 | 23 | 70 | 15.0 |

As shown in Table 1, in each Examples 1 to 12, which cured the resin with pressing to make the thickness of the resin layer be thinner than the average particle size of the particles, good electric conductivity was obtained even though loaded amounts of particles were not large; and a lighter biological electrode could be produced at lower cost since the loaded amount of the particles was smaller than Comparative Example 2. On the other hand, in Comparative Example 1, which cured the resin without pressing to make the thickness of the resin layer be thicker than the average particle size of the particles, the resistivity was extremely larger and the electric conductivity was inferior to that of Examples 1 to 12, although a light biological electrode could be produced at low cost since the loaded amount of the particles was almost equal to Examples 1 to 12. In Comparative Example 2, which loaded a large amount of particles and cured the resin without pressing to make the thickness of the resin layer be thicker than the average particle size of the particles, although the electric conductivity was as good as that of Examples 1 to 12, the large loaded amount of the particles caused increases of the weight and the production cost, together with lowering of the film strength.

As described above, it was revealed that the inventive biological electrode is superior in electric conductivity and biocompatibility, light in weight, and can be manufactured at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A method for manufacturing a biological electrode comprising:
    applying a composition comprising a resin and particles dispersed in the resin, the particles being coated with gold, silver, or platinum, onto an electro-conductive base material; and
    curing the resin under pressure;
    thereby forming a living body contact layer comprising the particles and a resin layer having a thickness equal to or thinner than an average particle size of the particles on the electro-conductive base material, wherein the particles constitute 0.5% or more and 70% or less in a volume ratio on a basis of a total volume of the formed resin layer and the particles, the resin is a silicon-containing resin having two or more moieties selected from a siloxane bond, an ester bond, an amide bond, an imide bond, an urethane bond, a thiourethane bond, and a thiol group, and a standard deviation of a particle size when measuring 10 pieces of the particles is 10% or less on a basis of an average particle size.

2. The method for manufacturing a biological electrode according to claim 1, wherein the average particle size of the particles is 1 μm or more and 1,000 μm or less, and the resin layer is formed to have a thickness of 0.5 μm or more and 1,000 μm or less.

3. The method for manufacturing a biological electrode according to claim 1, wherein the resin layer is formed to have a thickness with a ratio of the thickness to the average particle size of the particles being 0.5 or more and 1.0 or less.

4. The method for manufacturing a biological electrode according to claim 1, wherein the resin is at least one of a thermosetting resin and a photo-curable resin, and is cured by either or both of heat and light.

5. The method for manufacturing a biological electrode according to claim 1, wherein the resin is one or more resins selected from a silicone resin, a silicon atom-containing polyacrylic resin, a silicon atom-containing polyamide resin, a silicon atom-containing polyimide resin, a silicon atom-containing polyurethane resin, and a silicon atom-containing polythiourethane resin.

6. The method for manufacturing a biological electrode according to claim 1, wherein the electro-conductive base material comprises one or more species selected from gold, silver, silver chloride, platinum, aluminum, magnesium, tin, tungsten, iron, copper, nickel, titanium, stainless, and carbon.

7. The method for manufacturing a biological electrode according to claim 1, wherein the particles are spherical particles.

8. The method for manufacturing a biological electrode according to claim 1, wherein the particles are resin particles coated with gold, silver, or platinum, the resin particles comprising one or more resins selected from polyacrylate, polyethylene, polypropylene, polystyrene, polydivinylbenzene, novolac, and polyurethane.

9. The method for manufacturing a biological electrode according to claim 1, wherein the particles each have an electro-conductive metal layer comprising one or more electro-conductive metals selected from silver, aluminum, copper, nickel, tungsten, and tin in an interior of the particle.

10. The method for manufacturing a biological electrode according to claim 1, wherein the resin layer is formed to have a thickness thinner than the average particle size of the particles, and the particles are exposed convexly from a surface of the resin layer.

11. The method for manufacturing a biological electrode according to claim 1, wherein the particles are disposed such that each of the particles is the only particle in a thickness direction of the resin layer.

* * * * *